United States Patent [19]

Harvey

[11] 4,305,928
[45] Dec. 15, 1981

[54] DENTRIFICES

[75] Inventor: Kenneth Harvey, Wilmslow, England

[73] Assignee: Colgate-Palmolive Co., New York, N.Y.

[21] Appl. No.: 214,552

[22] Filed: Dec. 9, 1980

Related U.S. Application Data

[62] Division of Ser. No. 37,598, May 10, 1979, Pat. No. 4,263,276.

[30] Foreign Application Priority Data

May 19, 1978 [GB] United Kingdom ............... 20759/78

[51] Int. Cl.³ ............................................. A61K 7/18
[52] U.S. Cl. .................................... 424/52; 426/250; 426/540; 424/7; 424/49
[58] Field of Search ................................ 424/7, 52

[56] References Cited

U.S. PATENT DOCUMENTS

| | | | |
|---|---|---|---|
| 396,192 | 1/1889 | Clark | 424/58 |
| 1,947,635 | 2/1934 | Bergve | 424/49 |
| 3,451,824 | 6/1969 | McLeod | 426/250 |
| 3,538,230 | 11/1970 | Pader et al. | 424/50 |
| 3,678,155 | 7/1972 | Clippingdale | 424/52 |
| 3,689,637 | 9/1972 | Pader | 424/52 |
| 3,734,747 | 5/1973 | De Felice | 426/540 |
| 3,878,938 | 4/1975 | Venables et al. | 206/84 |
| 3,886,294 | 5/1975 | Emodi et al. | 426/540 |
| 3,903,252 | 9/1975 | Stearns et al. | 424/7 |
| 3,934,002 | 1/1976 | Haefele | 424/54 |
| 3,939,261 | 2/1976 | Barth | 424/49 |
| 3,939,283 | 2/1976 | Billington | 426/250 |
| 3,976,797 | 8/1976 | Furia | 426/540 X |
| 4,034,076 | 7/1977 | Coulson et al. | 424/49 |
| 4,071,615 | 1/1978 | Barth | 424/52 |
| 4,098,878 | 7/1978 | Baines et al. | 424/52 |
| 4,115,595 | 9/1978 | Jordan | 426/250 |
| 4,118,471 | 10/1978 | Pensak | 424/52 |
| 4,132,771 | 1/1979 | Schreiber et al. | 424/52 |
| 4,132,793 | 1/1979 | Haber et al. | 426/250 |
| 4,141,969 | 2/1979 | Mitchell | 424/52 |
| 4,263,276 | 4/1981 | Harvey | 424/52 |

FOREIGN PATENT DOCUMENTS

| | | |
|---|---|---|
| 2034562 | 1/1972 | Fed. Rep. of Germany . |
| 2602402 | 7/1976 | Fed. Rep. of Germany . |
| 2170018 | 9/1973 | France . |
| 2347039 | 4/1977 | France . |
| 47-14891 | 5/1972 | Japan . |
| 48-1509 | 1/1973 | Japan . |
| 51-31726 | 3/1976 | Japan . |
| 52-70048 | 6/1977 | Japan . |
| 52-122635 | 10/1977 | Japan . |
| 52-125668 | 10/1977 | Japan . |
| 52-145046 | 12/1977 | Japan . |
| 1384375 | 2/1975 | United Kingdom . |
| 1537252 | 12/1978 | United Kingdom . |

OTHER PUBLICATIONS

Warner-Jenkinson, 1969 Mfg. Broch. Certified Food Colors, 16 pp.
Kinnison Color Additives, 4 pp., Reprint from Packer/Processor, Jun. 1968.
Warner-Jenkinson, Jun. 1963 Pamphlet Coloring Cocktail Cherries, 6 pp.
Kitson et al., Food Technology 9(11):582-584, Nov. 1955 Metallic Discoloration of Candied Fruits.
Cohle et al., Food Industries, 23:91-93, Mar. 1951, Phytates Will Stop Cherry Discoloration.

*Primary Examiner*—Shep K. Rose
*Attorney, Agent, or Firm*—Herbert S. Sylvester; Murray M. Grill; Robert L. Stone

[57] ABSTRACT

An additive, 0.05% to 5% of phytic acid, a chelator, unlike other chelators such as tartaric acid or ethylene diamine tetra acetic acid, prevents or reduces color fading of from 0.0007% to 0.5% of a water-soluble non-toxic red or yellow monoazo or blue triarylmethane dye-colored visually clear dentrifice containing both alkali metal monofluorophosphate in an amount to provide from 0.01% to 1% of fluorine and from 5% to 50% of a selected siliceous polishing agent having an index of refraction between 1.44 and 1.47, in a liquid vehicle having an index of refraction matching that of said siliceous polishing agent.

10 Claims, No Drawings

DENTRIFICES

This is a division of application Ser. No. 037,598 filed May 10, 1979, now U.S. Pat. No. 4,263,276.

This invention relates to dentifrices.

Dentifrices which are coloured with a water-soluble dye have gained wide commercial acceptance, both for opaque dentifrices and transparent or translucent dentifrices. However, the dye is often not stable and the colour may fade with the passage of time.

The transparent and translucent dentifrices are commonly made using a siliceous material such as a colloidal or precipitated silica or sodium aluminosilicate as a polishing agent. Such material has an index of refraction to which the index of refraction of the dentifrice base can readily be matched, e.g. between 1.44 and 1.47. If desired, dentifrices containing the siliceous material as a polishing agent can be opacified by including a pigment such as titanium dioxide in minor amount in the dentifrice.

When dentifrices containing a siliceous polishing agent and an alkali metal fluoride or monofluorophosphate, such as sodium fluoride or sodium monofluorophosphate, are dyed, e.g. blue, green or red, the colour tends to fade.

This invention enables colour fading of dyed dentifrices containing a siliceous polishing agent and an alkali metal fluoride or monofluorophosphate to be reduced.

According to the invention a dentifrice comprises a dentifrice vehicle containing from 5% to 50% of a siliceous polishing agent having an empirical $SiO_2$ content of at least 70%, a particle size in the range from 1 to 35 microns, preferably from 2 to 20 microns, substantially amorphous X-ray structure and an index of refraction between 1.44 and 1.47; a compound which provides fluorine in amount to provide from 0.01% to 1% of fluorine, selected from alkali metal fluoride and alkali metal monofluorophosphate; from 0.0007% to 0.05% of a water-soluble non-toxic red or yellow monoazo dye or blue triarylmethane dye; and from 0.05% to 0.5% of an additive which prevents or reduces colour fading which is benzoic acid and/or phytic acid when alkali metal monofluorophosphate is present and which is benzoic acid when alkali metal fluoride is present.

All percentages are by weight of the dentifrice unless otherwise stated, and parts are by weight.

The proportion of the polishing agent of high silica content is in the range from 5% to 50% of the dentifrice, preferably from 10% to 30% such as from 15% to 25%. One abrasive is an amorphous alkali metal or alkaline earth metal aluminosilicate having a refractive index of from 1.44 to 1.47 and containing at least 70% silica, up to 10% alumina, up to 20% of moisture and up to 10% of sodium oxide. Typically, this material has a particle size in the range from 1 to 35 microns, preferably from 2 to 20 microns, e.g. 2 to 4 microns. The preferred moisture content is from 10% to 20% measured by ignition at 1000° C. and the typical content of sodium oxide is from 5% to 10%. Generally, the polishing agent has a loose bulk density of up to 0.2 g/cc, such as from 0.07 to 0.12 g/cc. Another suitable type of polishing agent is porous amorphous silicic anhydride having an average particle size preferably below 20 microns and above 1 micron, a surface area of at least 200 $m^2/g$, preferably at least 300 $m^2/g$, and a bulk density of at least 0.15 $g/cm^3$, preferably at least 0.30 $g/cm^3$, such as a dehydrated silica hydrogel (i.e. a xerogel), preferably of the well known regular density or intermediate density type. Examples of such amorphous silicic anhydride polishing agents are "Syloid 63", "Syloid 72" and "Syloid 74" (SYLOID is a trade mark) which are described in "The Davison Family of Syloid Silicas" published by their manufacturer, Grace, Davison Chemical Company. "Santocel 100" of Monsanto (SANTOCEL is a trade mark), is also a suitable dental abrasive. "Syloid 72" has an average particle size of about 4 microns, a surface area of about 340 $m^2/g$ and a bulk density of about 1.77 $g/cm^3$. For "Syloid 63" the corresponding figures are about 9 microns, about 675 $m^2/g$ and about 0.4 $g/cm^3$. A grade of "Santocel 100" has a surface area of about 239 $m^2/g$ and a bulk density of about 0.24 $g/cm^3$. These amorphous silicic anhydrides may be used singly or in mixtures.

The dentifrices of the present invention also contain an alkali metal fluoride or an alkali metal monofluorophosphate as a fluorine-containing compound having a beneficial effect on the care and hygiene of the oral cavity, e.g. diminution of enamel solubility in acid and protection of the teeth against decay. Examples include sodium fluoride, potassium fluoride, sodium monofluorophosphate and potassium monofluorophosphate. These materials, which dissociate or release fluorine-containing ions in water, are present in an effective non-toxic amount to provide within the range from 0.01% to 1% of the water-soluble fluorine content thereof.

Food-grade dyes are commonly used to colour dentifrices. Such dyes are water-soluble and non-toxic. Many of the red and yellow dyes are characterised by having a monoazo moiety and blue dyes by having a triarylmethane moiety. Such dyes include Amaranth (F.D. and C Red No. 2); Ponceau 4R (Food Red No. 7); Red 2 G (Food Red No. 10); Carmosine (Food Red No. 3); F.D. and C Yellow No 6; Edicol Supra Tartarizine N (F.D. and Yellow No. 5); F.D. and C Blue 1; Patent Blue. Such dyes are identified further in the Colour Index. They are employed in sufficient amount to provide desired coloured quality to the dentifrice, namely from 0.0007% to 0.05% of the dentifrice. Typically they are incorporated in the dentifrice in dilute aqueous solution, e.g. from 0.1% to 10% dye in water, preferably from 0.5% to 5%; the preferred amount of dye in the dentifrice is from 0.0007% to 0.006%. Most preferably, red or yellow dye is used in from 1% to 5% solution and in amounts in the range from 0.002% to 0.006% of the dentifrice, and blue dye is used in from 0.5% to 1% solution and in amounts in the range from 0.0007% to 0.002% of the dentifrice.

Benzoic acid and phytic acid have been found to stabilize the colour quality of the dyed dentifrice when alkali metal monofluorophosphate is present, and benzoic acid does so when alkali metal fluoride is present. Benzoic acid is an antioxidant and phytic acid is a chelator. However, antioxidants such as ascorbic acid and chelators such as tartaric acid and ethylene diamine tetracetic acid do not have a similar ability to stabilize colour quality of siliceous dentifrices containing a fluorine-providing agent. It is noteworthy that lesser amounts of phytic acid appear to be more effective in reducing colour fading than greater amounts in dentrifices containing alkali metal monofluorophosphate. Desired amounts of the additive are from 0.05% to 0.5%, preferably from 0.1% to 0.4% of benzoic acid (most preferably from 0.1% to 0.2%), and preferably from 0.05% to 0.3% of phytic acid.

Some grades of siliceous polishing materials are not compatible with an unlined aluminium toothpaste container. Benzoic acid and phytic acid possess the additional advantage that they render dentifrices containing such grades of siliceous polishing material compatible with unlined aluminium toothpaste containers.

The dentifrice is typically a toothpaste containing a gel or liquid vehicle, preferably as a mass of a consistency which can be extruded from a collapsible tube such as an aluminium tube or a lead tube. The vehicle contains liquid and solids. In general, the liquid portion comprises water, glycerine or sorbitol, including suitable mixtures thereof. It is usually advantageous to use a mixture of water and a humectant such as glycerine or aqueous sorbitol or polyethylene glycol. The total liquid content is generally in the range from 20% to 94.44% of a visually clear dentifrice, and typically comprises 0 to 30% of water, 0 to 80% of glycerine and 0 to 80% of sorbitol. Preferably, 0 to 20% of water, from 15% to 40% of glycerine and 0 to 50% of sorbitol are present in the dentifrice.

In the liquid portion of the vehicle, sorbitol is suitably employed as a 70% aqueous solution which has a refractive index of 1.45. Glycerine alone or admixed with the sorbitol solution does not substantially alter this desirable refractive index since glycerine has a refractive index of 1.47. Thus, an aqueous mixture of sorbitol and a substantial amount of glycerine gives an eminently satisfactory match to the refractive index of the polishing agent.

The solid portion of the vehicle is a gelling agent such as a natural or synthetic gum or gum-like material, such as Irish Moss, gum tragacanth, alkali metal carboxymethyl cellulose, hydroxyethyl carboxymethyl cellulose, polyvinyl pyrrolidone, starch, water-soluble hydrophilic colloidal carboxyvinyl polymer such as those sold as "Carbopol 934" and "Carbopol 940" (CARBOPOL is a trade mark), and synthetic inorganic silicated clays such as those sold as "Laponite CP" and "Laponite SP" (LAPONITE is a trade mark). These grades of "Laponite" have the formula $(Si_8Mg_{5.1}Li_{0.6}O_{24})^{0.6-}Na^+_{0.6}$. The solid portion of the vehicle is typically present in an amount up to 10% of the dentifrice, preferably from 0.5% to 5%. When employed, grades of "Laponite" are preferably used in amounts of from 1% to 5%.

Organic surface-active agents may be present in the dentifrices of the invention for increased prophylactic action, and to assist in achieving thorough and complete dispersion of the dentifrice throughout the oral cavity. The organic surface-active agents may be anionic, nonionic, ampholytic or cationic in nature, and it is preferred to employ as the surface-active agent a detersive material which imparts to the composition detersive and foaming properties. Suitable types of such detergents are water-soluble higher fatty acid monoglyceride monosulphates, such as the sodium salts of the monosulphated monoglyceride hydrogenated coconut oil fatty acids, higher alkyl sulphates, such as sodium lauryl sulphate, alkyl aryl sulphonates, such as sodium dodecyl benezene sulphonate, olefin sulphonates, such as sodium olefin sulfate in which the olefin group contains 12 to 21 carbon atoms, higher alkyl sulphonacetates, higher fatty acid esters of 1,2-dihydroxy propane sulphonates, and substantially saturated higher aliphatic acyl amides of lower aliphatic amino carboxylic acid compounds, such as those having 12 to 16 carbons in the fatty acid, alkyl or acyl radicals. Examples of the last mentioned amides are N-lauroyl sarcosine, and the sodium, potassium, and ethanolamine salts of N-lauroyl, N-myristoyl or N-palmitoyl sarcosine which should be substantially free from soap or similar higher fatty acid material which tends to reduce substantially the effect of these compounds. The use of these sarcosine compounds in dentifrices of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Other particularly suitable surface-active materials include nonionic agents such as condensates of one mole of sorbitan monostearate with approximately 60 moles of ethylene oxide, condensates of ethylene oxide with propylene oxide condensates of propylene glycol ("Pluronics"—PLURONIC is a trade mark) and amphoteric agents such as quaternized imidazol derivatives, which are available as "Miranol C₂M" (MIRANOL is a trade mark). Cationic surface-active germicides and antibacterial compounds such as di-isobutyl-phenoxyethoxyethyl dimethyl benzyl ammonium chloride, benzyl dimethyl stearyl ammonium chloride, tertiary amines having one fatty alkyl group (of from 12 to 18 carbon atoms) and two (poly) oxyethylene groups attached to the nitrogen (typically containing a total of from 2 to 50 ethanoxy groups per molecule) and salts thereof with acids, and compounds of the structure:

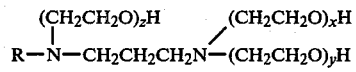

wherein R is a fatty alkyl group containing from 12 to 18 carbon atoms, and x, y and z total 3 or higher, as well as salts thereof with mineral or organic acids, may also be used. It is preferred to use from 0.05% to 5% of the foregoing surface-active materials in the dentifrices.

Any suitable flavouring or sweetening materials may be employed in formulating a flavour for the dentifrices. Examples of suitable flavouring constituents include flavouring oils, e.g. oils of spearmint, peppermint, wintergreen, sassafras, clove, sage, eucalyptus, majoram, cinnamon, lemon and orange, as well as methylsalicylate. Suitable sweetening agents include sucrose, lactose, maltose, sorbitol, dipeptides, as described in U.S. Pat. No. 3,939,261, oxathiazin salts as described in U.S. Pat. No. 3,932,606, perillartine and saccharine. Suitably, flavour and sweetening agents may together constitute from 0.01% to 5% or more of the dentifrice. Chloroform may also be used.

Various other adjuvant materials may be incorporated in the dentifrices of this invention. Examples are opacifying pigments if opacity is desired, preservatives, silicones, chlorophyll compounds, and ammoniated materials such as urea, diammonium phosphate and mixtures thereof. The adjuvants are incorporated in the dentifrices in amounts which do not substantially adversely affect the properties and characteristics desired.

Antibacterial agents may also be employed in the dentifrices of the invention, e.g. in an amount in the range from 0.01% to 5% by weight. Typical antibacterial agents include:

$N^1$-(4-chlorobenzyl)-$N^5$-(2,4-dichlorobenzyl) biguanide;

p-chlorophenyl biguanide;
4-chlorobenzylhydryl biguanide;
4-chlorobenzylhydrylguanylurea;
N-3-lauroxypropyl-N$^5$-p-chlorobenzylbiguanide;
1,6-di-p-chlorophenylbiguanidohexane;
1,6-bis(2-ethylhexylbiguanido) hexane;
1-(lauryldimethylammonium)-8-(p-chlorobenzyldimethylammonium) octane dichloride;
5,6-dichloro-2-guanidinobenzimidazole;
N$^1$-p-chlorophenyl-N$^5$-laurylbiguanide;
5-amino-1,3-bis(2-ethylhexyl)-5-methylhexahydropyrimidine;
and their non-toxic acid addition salts.

Synthetic finely divided silicas such as those sold as the "Cab-O-Sil M-5", "Syloid 244", "Syloid 266", "Aerosil D200" and mixtures thereof, may also be employed, e.g. in amounts of from 0.5% to 20%, to promote thickening or gelling and to improve clarity of the dentifrice (CAB-O-CIL, SYLOID and AEROSIL are trade marks).

A toothpaste dentifrice may be prepared by forming a gel with humectant, gum or thickener and sweetener and adding thereto polishing agent surface active agent and water.

The dentifrices should have a pH practicable for use, e.g. in the range from 3.2 to 10. A moderately acid to neutral pH is preferred, e.g. from 4.2 to 7.

The following Examples illustrate the invention.

EXAMPLE 1

The following red dyed clear dentifrice is prepared and deaerated and placed in lined and unlined aluminum tubes:

| COMPONENTS | PARTS |
|---|---|
| Glycerine | 25.00 |
| Sodium carboxymethyl cellulose | 0.20 |
| Sodium saccharin | 0.17 |
| Sorbitol (70% solution) | 41.56 |
| Water - deionised | 3.00 |
| Amaranth and F,D & C Yellow No. 5 4:1 mixture (5% solution) | 0.15 |
| Benzoic acid | 0.10 |
| Sodium monofluorophosphate | 0.82 |
| Sodium aluminosilicate | 17.00 |
| Silica thickener ("Syloid 244") | 6.00 |
| Sodium lauryl sulphate | 2.00 |
| Flavour | 1.00 |
| pH - 5.77 | |

Upon aging for three months at room temperature, at 43° C. and at 4° C., no substantial fading of the Amaranth- F, D and C Yellow No. 5 dyed dentifrice is observed. The formulations remain compatible with their tubes and fluoride retention is high.

EXAMPLE 2

Similar results are observed when the formula of Example 1 is modified to employ (a) 0.15 parts benzoic acid and 44.51 parts sorbitol (70%) and (b) 0.20 parts benzoic acid and 44.46 parts sorbitol (70%). The pH values of dentifrices (a) and (b) are 5.55 and 5.37, respectively.

EXAMPLE 3

Similar results of colour stability are observed when 0.10 part, 0.15 part and 0.20 part of benzoic acid are incorporated in the following red dyed clear deaerated dentifrice formulation and placed in unlined aluminium tubes:

| COMPONENT | PARTS |
|---|---|
| Glycerine | 25.00 |
| Sodium carboxymethyl cellulose | 0.18 |
| Sodium saccharin | 0.17 |
| Sodium monofluorophosphate | 0.82 |
| Sorbitol (70% solution) | 40.48 less indicated amount of benzoic acid |
| Water - dionised | 3.00 |
| Polyethylene glycol 600 | 3.00 |
| Amaranth and F, D and C Yellow No. 5 - 4:1 mixture (5% solution) | 0.15 |
| Silica thickener ("Syloid 244") | 7.20 |
| Sodium aluminosilicate | 17.00 |
| Flavour | 1.00 |
| Sodium lauryl sulphate | 2.00 |

The pH values of these dentifrices with 0.10 part, 0.15 part and 0.20 part of benzoic acid are 5.59, 5.37 and 5.22, respectively.

EXAMPLE 4

Two yellow dyed dentifrices similar to Example 3, but containing 0.2 part of benzoic acid and in one case 0.1 part and 0.5 part of F, D and C Yellow No. 5 and in the other case 0.5 part of F, D, C Yellow No. 6 (pH 5.5 and 5.6, respectively) are stable against colour fading upon aging.

EXAMPLE 5

The following red dyed clear dentifrices are prepared deaerated and placed in unlined aluminium tubes:

| COMPONENTS | PARTS A | B | C | D |
|---|---|---|---|---|
| Glycerine | 25.00 | 25.00 | 25.00 | 25.00 |
| Sodium carboxymethyl cellulose | 0.19 | 0.19 | 0.19 | 0.19 |
| Sodium saccharin | 0.17 | 0.17 | 0.17 | 0.17 |
| Sodium monofluorophosphate | 0.82 | 0.82 | 0.82 | 0.82 |
| Sorbitol (70% solution) | 41.57 | 41.37 | 41.17 | 41.67 |
| Water - deionized | 3.00 | 3.00 | 3.00 | 3.00 |
| Polyethylene glycol 600 | 3.00 | 3.00 | 3.00 | 3.00 |
| Amaranth and F, D & C Yellow No. 5 4:1 mixture (5% solution) | 0.15 | 0.15 | 0.15 | 0.15 |
| Phytic acid | 0.10 | 0.30 | 0.50 | — |
| Sodium aluminosilicate | 17.00 | 17.00 | 17.00 | 17.00 |
| Silica thickener (Syloid 244) | 6.00 | 6.00 | 6.00 | 6.00 |
| Sodium lauryl sulphate | 2.00 | 2.00 | 2.00 | 2.00 |
| Flavour | 1.00 | 1.00 | 1.00 | 1.00 |
| pH | 5.48 | 4.74 | 4.22 | 6.20 |

The dentifrices are aged at room temperature and 43° C. Formulations A and B are compatible while gassing occurs after three months at 43° C. with formulation C containing 0.50 parts by phytic acid. No substantial colour fading occurs with formulations A and B. With formulation C there is slight colour fading at room temperature and somewhat more at 43° C. The red disappears at room temperature and at 43° C. with formulation D.

EXAMPLE 6

Example 3 is repeated with (a) 0.05 part (pH 5.41); (b) 0.10 part (pH 5.09); (c) 0.30 part (pH 4.25) and (d) 0.50 part (pH 3.26) of phytic acid used instead of benzoic acid. No substantial colour fading is observed.

EXAMPLE 7

The following blue dyed opacified dentifrices are prepared, deaerated and placed in lined and unlined aluminium tubes.

| COMPONENTS | PARTS | | | |
|---|---|---|---|---|
| | A | B | C | D |
| Glycerine | 25.00 | 25.00 | 25.00 | 25.00 |
| Sodium carboxymethyl cellulose | 0.18 | 0.18 | 0.18 | 0.18 |
| Sodium saccharin | 0.17 | 0.17 | 0.17 | 0.17 |
| Titanium dioxide | 1.00 | 1.00 | 1.00 | 1.00 |
| Sorbitol (70% solution) | 40.59 | 40.54 | 40.49 | 40.17 |
| Water - deionised | 3.00 | 3.00 | 3.00 | 3.00 |
| Polyethylene glycol 600 | 3.00 | 3.00 | 3.00 | 3.00 |
| Patent Blue dye (0.5% solution) | 0.14 | 0.14 | 0.14 | 0.14 |
| Sodium monofluorophosphate | 0.82 | 0.82 | 0.82 | 0.82 |
| Benzoic acid | 0.10 | 0.15 | 0.20 | — |
| Sodium aluminosilicate | 17.00 | 17.00 | 17.00 | 17.00 |
| Silica thickener ("Syloid 244") | 6.00 | 6.00 | 6.00 | 6.50 |
| Sodium lauryl sulphate | 2.00 | 2.00 | 2.00 | 2.00 |
| Flavour | 1.00 | 1.00 | 1.00 | 1.00 |
| pH | 5.66 | 5.49 | 5.36 | 6.79 |

The dentifrices are aged at room temperature, at 43° C. and at 4° C. Formulation A with 0.10 part of benzoic acid exhibits substantially no colour fade except in the cases of 3 months aging at room temperature and 1 month aging at 43° C. whereat very slight fading is observed with the unlined aluminium tubes, and 3 months aging at 43° C. whereat slight fading is observed with both lined and unlined tubes.

Formulation B with 0.15 part of benzoic acid exhibits substantially no fade, even after 3 months aging at 43° C., although very slight fading with the unlined aluminium tubes is observed in an earlier observation after 1 month aging at 43° C.

Formulation C with 0.20 part of benzoic acid exhibits substantially no fade except after 3 months aging at 43° C. with the lined aluminium tubes, whereat slight fading is seen.

Each of formulations A, B and C are compatible with their tubes and exhibit high fluoride retentions.

Formulation D, with no additive, exhibits slight colour fading with unlined aluminium tubes after 3 months aging at 4° C. and is substantially or slightly faded with unlined aluminium tubes after 1, 3 and 6 months aging at room temperature and after 2 weeks, 1 month and 3 months aging at 43° C. Further, tube incompatibility is observed with unlined tubes after 1, 3 and 6 months aging at room temperature and after 1 and 3 months aging at 43° C.

In addition to the substantial problems with the formulation D of Example 4 and Formulation D of Example 6, the colour is not stable when the additives added to red dyed clear dentifrices are: from 0.25% to 0.01% tartaric acid, from 0.25% to 0.01% ethylene diamine tetraacetic acid, and from 0.20% to 2% ascorbic acid.

EXAMPLE 8

The following dentifrices are substantially stable against colour fading upon aging:

| COMPONENTS | PARTS | | | | | | | |
|---|---|---|---|---|---|---|---|---|
| | A | B | C | D | E | F | G | H |
| Glycerine | 25.00 | 25.00 | 25.00 | 25.00 | 25.00 | 25.00 | 25.00 | 25.00 |
| Sodium carboxymethylcellulose | 0.19 | 0.19 | 0.19 | 0.19 | 0.19 | 0.19 | 0.19 | 0.19 |
| Sodium saccharin | 0.17 | 0.17 | 0.17 | 0.17 | 0.17 | 0.17 | 0.17 | 0.17 |
| Sorbitol (70% solution) | 41.90 | 41.50 | 42.10 | 42.05 | 41.70 | 42.15 | 42.10 | 42.05 |
| Water-deionised | 3.00 | 3.00 | 3.00 | 3.00 | 3.00 | 3.00 | 3.00 | 3.00 |
| Polyethylene glycol 600 | 3.00 | 3.00 | 3.00 | 3.00 | 3.00 | 3.00 | 3.00 | 3.00 |
| Dye (as indicated) | 0.30 | 0.70 | 0.10 | 0.15 | 0.50 | 0.15 | 0.15 | 0.15 |
| Sodium fluoride | 0.24 | 0.24 | 0.24 | 0.24 | 0.24 | 0.24 | 0.24 | 0.24 |
| Benzoic acid | 0.20 | 0.20 | 0.20 | 0.20 | 0.20 | 0.20 | 0.20 | 0.20 |
| Sodium aluminosilicate | 17.00 | 17.00 | 17.00 | 17.00 | 17.00 | 17.00 | 17.00 | 17.00 |
| Silica thickener ("Syloid 244") | 6.00 | 6.00 | 6.00 | 6.00 | 6.00 | 6.00 | 6.00 | 6.00 |
| Sodium lauryl sulphate | 2.00 | 2.00 | 2.00 | 2.00 | 2.00 | 2.00 | 2.00 | 2.00 |
| Flavour | 1.00 | 1.00 | 1.00 | 1.00 | 1.00 | 1.00 | 1.00 | 1.00 |
| pH | 6.6 | 6.7 | 6.1 | 7.0 | 6.9 | 6.4 | 6.2 | 6.0 |

The following dyes are used in the above dentifrices:
A—0.50% solution of patent blue;
B—1% solution of carmosine;
C—5% solution of F, D and C Yellow No. 5;
D—1% solution of F, D and C Blue No. 1;
E—1% solution of F, D and C Yellow No. 6;
F—4:1 mixture of 5% solution of Amaranth and F, D and C Yellow No. 5;
G—4:1 mixture of 5% solution of Amaranth and F, D and C Yellow No. 5;
H—4:1 mixture of 5% solution of Amaranth and F, D and C Yellow No. 5.

What we claim is:

1. A visually clear dentifrice comprising a dentifrice vehicle containing from 5% to 50% of a siliceous polishing agent having an empirical $SiO_2$ content of at least 70%, a particle size in the range from 1 to 35 microns, a substantially amorphous X-ray structure and an index of refraction between 1.44 and 1.47; a liquid vehicle having an index of refraction matching that of said siliceous polishing agent; alkali metal monofluorophosphate in amount to provide from 0.01% to 1% of fluorine; from 0.0007% to 0.5% of a water-soluble nontoxic red or yellow monoazo dye or blue triarylmethane dye; and from 0.05% to 5% of phytic acid as an additive which prevents or reduces colour fading.

2. A dentifrice as claimed in claim 1 wherein the siliceous polishing agent has a particle size in the range from 2 to 20 microns.

3. A dentifrice as claimed in claim 1 wherein the polishing agent is sodium aluminosilicate which is present in amount in the range from 15% to 25%.

4. A dentifrice as claimed in claim 1 wherein the compound which provides fluorine is sodium monofluorophosphate.

5. A dentifrice as claimed in claim 1 wherein phytic acid is present in amount from 0.05% to 0.30%.

6. A dentifrice as claimed in claim 1 wherein the dye is a monoazo dye which dyes the dentifrice red.

7. A dentifrice as claimed in claim 1 wherein the dye is a monoazo dye which dyes said dentifrice yellow.

8. A dentifrice as claimed in claim 1 wherein the dye is a mixture of amaranth and F, D and C Yellow No 5.

9. A dentifrice as claimed in claim 1 wherein the dye is a triarylmethane dye which dyes the dentifrice blue.

10. A dentifrice as claimed in claim 1 contained in an unlined aluminium container.

* * * * *